US009820927B2

(12) United States Patent
Hotz et al.

(10) Patent No.: US 9,820,927 B2
(45) Date of Patent: Nov. 21, 2017

(54) AQUEOUS OIL IN WATER MICRO-EMULSIONS, AND PRODUCT

(71) Applicant: Givaudan SA, Vernier (CH)

(72) Inventors: Jutta Hotz, Zürich (CH); Christian Quellet, Biel (CH)

(73) Assignee: GIVAUDAN SA, Vernier (CH)

( * ) Notice: Subject to any disclaimer, the term of this patent is extended or adjusted under 35 U.S.C. 154(b) by 161 days.

(21) Appl. No.: 14/361,926

(22) PCT Filed: Dec. 21, 2012

(86) PCT No.: PCT/EP2012/076564
§ 371 (c)(1),
(2) Date: May 30, 2014

(87) PCT Pub. No.: WO2013/092962
PCT Pub. Date: Jun. 27, 2013

(65) Prior Publication Data
US 2014/0371128 A1 Dec. 18, 2014

(30) Foreign Application Priority Data
Dec. 23, 2011 (GB) .................................. 1122235.3

(51) Int. Cl.
| | |
|---|---|
| *A61K 8/49* | (2006.01) |
| *A61K 8/34* | (2006.01) |
| *A61K 8/39* | (2006.01) |
| *A61Q 13/00* | (2006.01) |
| *A61Q 15/00* | (2006.01) |
| *A61K 8/92* | (2006.01) |
| *A61K 8/06* | (2006.01) |
| *A61K 8/60* | (2006.01) |

(52) U.S. Cl.
CPC ............ *A61K 8/4973* (2013.01); *A61K 8/068* (2013.01); *A61K 8/345* (2013.01); *A61K 8/39* (2013.01); *A61K 8/4993* (2013.01); *A61K 8/604* (2013.01); *A61K 8/922* (2013.01); *A61Q 13/00* (2013.01); *A61Q 15/00* (2013.01); *A61K 2800/30* (2013.01)

(58) Field of Classification Search
CPC .................................................... A61Q 13/00
See application file for complete search history.

(56) References Cited

U.S. PATENT DOCUMENTS

| | | | |
|---|---|---|---|
| 7,262,158 B1 * | 8/2007 | Lukenbach | .......... A61K 8/0208 510/119 |
| 2003/0186836 A1 | 10/2003 | Dumanois et al. | |
| 2005/0271598 A1 | 12/2005 | Friedman et al. | |
| 2009/0068219 A1 * | 3/2009 | Elie | ........................ A61Q 19/08 514/1.1 |
| 2011/0159104 A1 * | 6/2011 | Teslenko | ................ A23K 1/164 424/537 |

FOREIGN PATENT DOCUMENTS

| | | | | |
|---|---|---|---|---|
| DE | 19537509 A1 | 4/1997 | | |
| DE | 102008034944 A1 * | 1/2010 | ............. | A23K 1/164 |
| EP | 2340804 A1 | 7/2011 | | |
| FR | 2802810 A1 * | 6/2001 | ............. | A61K 8/361 |
| HU | 9602264 A1 * | 11/1997 | | |
| WO | 2005123028 A1 | 12/2005 | | |

OTHER PUBLICATIONS

English Machine Translation of FR2802810 A1 obtained Dec. 9, 2015 at http://worldwide.espacenet.com/publicationDetails/description?CC=FR&NR=2802810A1&KC=A1&FT=D&ND=3&date=20010629&DB=EPODOC&locale=en_EP.*
Arlatone Product Data Sheet obtained Dec. 9, 2015 at http://www.crodacropcare.com/home.aspx?d=content&view=dtl&s=143&r=256&p=1932&prodID=265.*
Definition of "Aqueous" from Dictionary.com obtained May 9, 2016.*
"Tabla de algunos HLB" obtained at https://www.scribd.com/doc/62416006/Tabla-Algunos-HLB on Jan. 4, 2017.*
Xalifin-15 Product Data Sheet obtained at http://www.in-cosmetics.com/_novadocuments/243295?v=636009925186430000 on Jan. 4, 2017.*
English Machine Translation of HU9602264A1 obtained from HCAPLUS on Dec. 8, 2015.*
English Translation of HU 215599. Obtained Apr. 2017. United States Patent and Trademark Office. Translated by FLS Inc.*
GB Search Report for application GB1122235.3 dated Apr. 20, 2012.
International Search Report and Written Opinion of the International Searching Authority for PCT/EP2012/076564 dated Oct. 20, 2014.

* cited by examiner

*Primary Examiner* — Lanee Reuther
(74) *Attorney, Agent, or Firm* — Norris McLaughlin & Marcus PA

(57) ABSTRACT

Disclosed are clear, aqueous perfume compositions which are free of ethanol. There is further provided a perfume composition which is clear, provides a good skin feeling, and good air drying properties on the skin.

7 Claims, No Drawings

AQUEOUS OIL IN WATER MICRO-EMULSIONS, AND PRODUCT

This is an application filed under 35 USC 371 of PCT/EP2012/076,564, filed 21 Dec. 2012, which in turn claims priority to GB 1122235.3 filed 23 Dec. 2011.

Provided are clear, aqueous perfume compositions which are free of ethanol. There is further provided a perfume composition which is clear, provides a good skin feeling, and good air drying properties on the skin.

In the fragrance industry there is a long standing need for ethanol-free perfume compositions due to the concerns about volatile organic compounds (VOCs), which are claimed to emit ground level ozone under certain extreme weather conditions. Perfume compositions intended for the application to the skin are commonly solubilised with ethanol or ethanol/water mixtures with a high content of ethanol.

The task to produce ethanol free perfume compositions, which resemble an ethanol-based perfume composition in terms of skin feeling and clarity of the composition, with good drying properties, is difficult.

Aqueous perfume compositions which are free of ethanol are known in the art. However, since most fragrances are substantially immiscible with water, in order to obtain clear formulations it is necessary to employ large amounts of surfactants as solubilising agents or to apply high shear forces to reach oil droplet sizes in a small micro-meter range like it is, for example, realized in emulsions.

Even though a lot of work has been done in this area, the formulations produced are not completely satisfactory and there remains a need for improved composition addressing the shortcomings in the prior art.

It has now been found that by using a unique combination of an odoriferous oil phase (i) and non-ionic surfactants (ii) in combination with particular co-solvents (iii) it is possible to obtain ethanol-free, clear perfumed compositions possessing a good skin feeling, which are less tacky, and have a high drying speed.

There is provided in a first aspect an aqueous micro-emulsion comprising
  i) an odoriferous oil phase
  ii) at least one non-ionic surfactant
  iii) at least one co-solvent selected from isosorbide, solketal, and ethers thereof, or mixtures thereof, and
  iv) optionally, one solubilizer selected from glycerol derivatives and diols.

The non-ionic surfactant, present in the micro-emulsion may be selected from broad range of commercially available products, and include C4-C22 alkyl ethoxylates with about 1-25 ethylene oxide units, including the so-called narrow peaked alkyl ethoxylates, particularly ethoxylates and mixed ethoxylates/propoxylates, alkyl dialkyl amine oxides, alkyl polyglycosides, alkanoyl glucose amides, and mixtures thereof. Specific examples of non-ionic surfactants are the condensation products of aliphatic alcohols with from about 1 to about 22 moles of ethylene oxide. The alkyl chain of the aliphatic alcohol can either be straight or branched, primary or secondary, and generally contains from about 8 to about 18 carbon atoms. Examples of commercially available non-ionic surfactants of this type include Tergitol™ marked by The Dow Chemical Corporation, such as Tergitol™ 15-S-9 (the condensation product of C11-C15 linear secondary alcohol with 9 moles ethylene oxide), and Tergitol™ 24-L-6 NMW (the condensation product of C12-C14 primary alcohol with 6 moles ethylene oxide with a narrow molecular weight distribution); Neodol® marked by Shell Chemical Company, e.g., Neodol® 45-9 (the condensation product of C14-C15 linear alcohol with 9 moles of ethylene oxide), Neodol® 23-6.5 (the condensation product of C12-C13 linear alcohol with 6.5 moles of ethylene oxide), Neodol® 45-7 (the condensation product of C14-C15 linear alcohol with 7 moles of ethylene oxide), and Neodol® 45-4 (the condensation product of C14-C15 linear alcohol with 4 moles of ethylene oxide); Kyro® EOB (the condensation product of C13-C15 alcohol with 9 moles ethylene oxide), marketed by The Procter & Gamble Company; Cosmacol® NII9 (the mixture of linear and mono branched C12-C13 with 9 moles of ethylene oxide), marketed by Sasol Olefins and Surfactants GmbH; Dehydol® series marketed by Cognis/BASF, preferably C8 to C18 (e.g. C10) with 2 to 14 moles of ethylene oxide, and mixtures thereof; Trideceth series, the condensation products of C13 alcohols and 2-21 moles of ethylene oxide, like Trideceth-9** and Trideceth-10.

Other commercially available non-ionic surfactants include Dobanol® 91-8 marketed by Shell Chemical Co., and Genapol® UD-080 marketed by Clariant. This category of non-ionic surfactant is referred to generally as "alkyl ethoxylates."

Other examples of non-ionic surfactants include the condensation products of ethylene oxide with a hydrophobic base formed by the condensation of propylene oxide with propylene glycol. Examples of compounds of this type include certain of the commercially-available Pluronic® surfactants, marketed by BASF, Eumulgin® L** marketed by Cognis/BASF (e.g. PPG-1-PEG-9 Lauryl Glycol Ether).

Further examples of non-ionic surfactants are the polyethylene glycol sorbitol ethers containing 3-30 EO units (including, for example, sorbitol esters with oleic, myristic, stearic, palmitic acid, and the like). They are also known under the trade name Tween, such as Tween 20**, Tween 40, and Tween 60.

Further examples of non-ionic surfactants are the condensation products of ethylene oxide (EO) with the product resulting from the reaction of propylene oxide and ethylene diamine. Examples of this type of non-ionic surfactants include certain of the commercially available Tetronic® compounds, marketed by BASF.

Semi-polar non-ionic surfactants are a special category of non-ionic surfactants which include water-soluble amine oxides. These amine oxide surfactants in particular include C10-C18 alkyl dimethyl amine oxides and C8-C12 alkoxy ethyl dihydroxy ethyl amine oxides.

Other non-ionic surfactants are alkyl polyglycosides including, for example, C8-C10 polyglycosides (e.g. Radia® Easysurf 6881, marketed by Oleon; Oramix™ CG110, marketed by Seppic), C12-C16 alkyl polyglycosides (e.g. Plantaren® 1200 NP, marketed by Cognis/BASF), C8-C16 alkyl polyglycosides (e.g. Plantaren® 2000 N UP, marketed by Cognis/BASF), C5 Amyl xyloside (Radia Easysurf 6505, marketed by Oleon) and mixture of C5 Amyl, C8 Capryl, C12 Lauryl xylosides (Radia Easysurf 6552, marketed by Oleon).

Further non-ionic surfactants include, for example, PEG 40 hydrogenated castor oil (Cremophor® RH 40 market by BASF), other types of the Cremophor® RH series, and PEG 400 (Lipoxol® marketed by Sasol Olefins and Surfactants GmbH).

The surfactants indicated with **, or mixtures thereof are especially preferred.

In a further embodiments, non-ionic surfactants are preferred, which posses almost no odour, i.e. they are essentially odourless. However, non-ionic surfactants which are not essentially odourless may contribute in a desired effect to the overall odour characteristics of a composition and thus also suitable.

In a further embodiment, there is provided an aqueous micro-emulsion wherein the non-ionic surfactant having a HLB (hydrophilic-lipophilic balance) of about 8 to 18.

As used herein, the term "surfactant" denotes for surface active agents, which possess a low volatility and, in contrary to ethanol, evaporate slowly from the emanating surface.

The solubilizer optionally present in the micro-emulsion may be selected from glycerol derivatives and diols, including vicinal and non-vicinal diols. Suitable diols may include diols comprising 3-12, preferably 3-8 carbon atoms. As examples one may cite 1,2-propanediol (propyleneglycol), 1,3-propanediol (ZEMEA™ marketed by Duponte Tate & Lyle), 1,2-pentandiol, 2-methyl-pentan-2,4-diol (Diolane) 1,2-hexanediol, 1,2-octanediol, dipropylene glycol propyl ether (Dowanol® DPnP marketed by Dow Chemicals), and dipropylene glycol isobornylether (Pribelance™ Clear marketed by CARB). The micro-emulsion of the present invention may comprise up to 10% by weight of a solubilizer, or a mixture of solubilizers.

As used herein, the term "solubilizer" is an ingredient which improves the solubilizing properties of the surfactant.

The co-solvent, present in the micro-emulsion is selected from isosorbide (hexahydrofuro[3,2-b]furan-3,6-diol; i.e. a compound of formula (B) wherein $R^2$ and $R^3$ are hydrogen), solketal ((2,2-dimethyl-1,3-dioxolan-4-yl)methanol; i.e. a compound of formula (A) wherein $R^1$ is hydrogen), and ethers thereof. The ether chain(s) may comprising 1 to 5 (e.g. 2, 3, or 4) carbon atoms. Suitable ethers of solketal include 4-(methoxymethyl)-2,2-dimethyl-1,3-dioxolane (1 carbon atom), and 4-(ethoxymethyl)-2,2-dimethyl-1,3-dioxolane (2 carbon atoms). Suitable ethers of isosorbide include 3,6-dimethoxyhexahydrofuro[3,2-b]furan.

In one embodiment the co-solvent, present in the micro-emulsion is selected from a compound of formula (A)

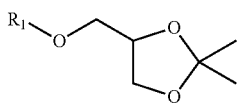

(A)

wherein $R^1$ is selected from hydrogen, methyl, ethyl, linear and branched $C_3$-$C_5$ alkyl, including $C_4$ alkyl, and $C_2$-$C_5$ hydroxy alkyl.

In another embodiment the co-solvent, present in the micro-emulsion is selected from a compound of formula (B)

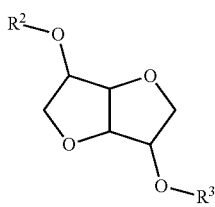

(B)

wherein $R^2$ and $R^3$ independently of each other are selected from hydrogen, methyl, ethyl, linear and branched $C_3$-$C_5$ alkyl (including $C_4$ alkyl), and $C_2$-$C_5$ hydroxy alkyl.

The term "odoriferous oil", present in the micro-emulsion, refers to one single olfactively active ingredient or a mixture of ingredients providing a pleasant smell and which are oil soluble. An olfactively active ingredient can be any natural oil or extract, or chemical compound used in a fragrance composition. Said ingredients are well known in the art and many are described in "Perfume and Flavour Chemicals", S. Arctander, Allured Publishing Corporation, 1994, IL, USA, which is incorporated herein by reference.

Examples of odoriferous oils are extracts of flowers (e.g. lily, lavender, rose, jasmine, neroli or ylang-ylang), stems and leaves (e.g. geranium, patchouli or petitgrain), fruits (e.g. anis, coriander, cumin or juniper), fruit skins (e.g. bergamot, citrus or orange), roots (e.g. macis, angelica, cardamom, iris or calmus) wood (e.g. pine, sandalwood, guaiac, cedar or rose), herbs and grasses (e.g. tarragon, lemon grass, salvia or thyme), needles and branches (e.g. pine or fir), resins and/or balms (e.g. galbanum, elemi, benzol, myrrh, olibanum or opoponax). Further, animal raw materials such as zibet and/or castoreum can be used as odoriferous oils according to the invention. Typical synthetic olfactively active ingredients are for instance compounds belonging to the chemical class of alcohols (e.g. cinnamic alcohol, cis-3-hexenol, citronellol, Ebanol™ (3-methyl-5-(2,2,3-trimethyl-3-cyclopenten-1-yl)-4-pentent-2-ol & isomers), eugenol, farnesol, geraniol, Javanol™ ([1-methyl-2-[(1,2,2-trimethylbicyclo[3.1.0]hex-3-yl)methyl] cyclopropyl]methanol), linalool, menthol, nerol, phenylethyl alcohol, rhodinol, Sandalore™ (3-methyl-5-(2,2,3-trimethylcyclopent-3-en-1-yl)pentan-2-ol), Super Muguet™ (6-ethyl-3-methyl-6(5)-octen-1-ol), terpineol or Timberol™ (1-(2,2,6-trimethylcyclohexyl)hexan-3-ol)), aldehydes and ketones (e.g. Azurone® (7-(3-methylbutyl)-1,5-benzodioxepin-3-one), anisaldehyde, α-amylcinnamaldehyde, Georgywood™ (1-(1,2,8,8-tetramethyl-1,2,3,4,5,6,7,8-octahydronaphthalen-2-yl)ethanone), hydroxycitronellal, Iso E® Super (1-(2,3,8,8-tetramethyl-1,2,3,4,5,6,7,8-octahydronaphthalen-2-yl)ethanone), Isoraldeine® (3-methyl-4-(2,6,6-trimethylcyclohex-2-en-1-yl) but-3-en-2-one), Hedione® (methyl 2-(3-oxo-2-pentylcyclopentyl)acetate), Lilial® (3-(4-(tert-butyl) phenyl)-2-methylpropanal), maltol, methyl cedryl ketone, methylionone, verbenone or vanillin), ethers and acetals (e.g. Ambrox™ (dodecahydro-3a,6,6,9a-tetramethylnaphtho[2,1-b]furan), geranyl methyl ether, rose oxide or Spirambrene™ (2',2',3,7,7-pentamethylspiro[bicycle[4.1.0] heptane-2,5'-[1,3]dioxane])), esters and lactones (e.g. benzyl acetate, cedryl acetate, γ-decalactone, Helvetolide® (2-(1-(3,3-dimethylcyclohexyl)ethoxy)-2-methylpropyl propionate), γ-undecalactone or vetivenyl acetate), macrocycles (e.g. Ambrettolide (oxacyclohepadec-10-en-2-one), ethylene brassylate or Exaltolide® (oxacyclohexadecan-2-one) and heterocycles such as isobutylquinoline.

In one embodiment the odoriferous oil phase may be a complex mixture of many ingredients, some may behave as additional solubilizers. For example, low alcohols such as hexanol, butanol, and pentanol are known to act as solubilizers or co-solvents, facilitating the spontaneous formation of micro-emulsions.

The quantity of the odoriferous oil phase in the micro-emulsion is largely determined by the intended use of the micro-emulsion. Particularly preferred are micro-emulsions comprising relatively high amounts of an odoriferous oil phase, preferably up to 15 weight percent based on the micro-emulsion. The micro-emulsions as defined above are mainly intended for direct use, e.g. perfuming the skin, fabric, hair, or air (as air fresheners, deodorants). However, they may also be incorporated into consumer products, such as cosmetic products (e.g. body deodorants), and hard surface cleaners, thus obtaining a fragranced product.

For the purpose of this invention by "micro-emulsion" is meant a thermodynamically stable liquid mixture of oil, water and surfactant in combination with a co-solvent.

The micro-emulsion may further contain other ingredients such as antioxidants, chelating agents, UV-filters, cooling agents, preservatives, thickening agents, cosmetic active ingredients, moisturizers, humectants, emollients, pigments, colorants, dyes, antifoams, pH adjusting or buffering agents, or other ingredients known to those skilled in the art.

The micro-emulsion as hereinabove described may be prepared according to methods known in the art.

Particular embodiments of the present invention are now further described with reference to the following non-limiting examples.

The examples are for the purpose of illustration only and it is to be understood that variations and modifications can be made by one skilled in the art without departing from the scope of the attached claims. It should be understood that the embodiments described may be used individually, or may be combined.

EXAMPLE 1

Several composition were prepared with the ingredients (amounts given in % by weight) listed in Table 1, as follows.

In a beaker equipped with a stirrer and at room temperature, all ingredients marked with (A) in Table 1 were mixed until they dissolved. To the resulting aqueous phase the odoriferous oil phase (marked with (B) in Table 1) was added with constant low stirring speed. Clear solutions were thus obtained.

Three freeze-thaw cycles were passed to control the reversibility of the micro-emulsion formation. All eight compositions successfully passed the freeze-thaw cycles, confirming that a micro-emulsion was obtained.

The formulations were subject to standard stability testing at 4 to 50° C.

EXAMPLE 2

TABLE 2

|  | Example | |
|---|---|---|
| Ingredient | 2-1 | 2-2 |
| odoriferous oil phase (B) | 12 | 10 |
| non-ionic surfactant (A) | | |
| Barsolve Plus[1] | 16 | 12 |
| Solubilizer (A) | | |
| 1,2 Hexanediol | — | 7 |
| Co-solvent (A) | | |
| Solketal | 7 | 6 |
| Water (A) | 65 | 65 |

The compositions 2-1 and 2-2 (amounts given in % by weight) were prepared following the general procedure as described in Example 1 and tested under the same conditions. Both successfully passed the freeze-thaw cycles, confirming that a micro-emulsion was obtained.

EXAMPLE 3

The compositions were evaluated by 19 panelists in blind by comparison of two compositions. The compositions were sprayed onto each of the forearms of the panelist and evaluated over a period of 8 hours. Each panelist was asked to the sensory properties as indicated in Table 3 below and the drying time.

TABLE 1

| | Example | | | | | | | |
|---|---|---|---|---|---|---|---|---|
| Ingredient | 1-1 comparison | 1-2 | 1-3 | 1-4 | 1-5 | 1-6 | 1-7 | 1-8 |
| odoriferous oil phase (B) | 8 | 8 | 8 | 8 | 8 | 8 | 8 | 8 |
| non-ionic surfactant (A) | | | | | | | | |
| Barsolve Plus[1] | 10 | 8 | 8 | 8 | 8 | — | 14 | — |
| Radia Easysurf 6881[2] | — | — | — | 5 | — | — | — | — |
| Oramix[3] | — | — | — | — | 2 | — | — | — |
| Eumulgin L[4] | — | — | — | — | — | 14 | — | — |
| Cremophor ® RH 40[5] | — | — | — | — | — | — | — | 12 |
| Solubilizer (A) | | | | | | | | |
| 1,2 Hexanediol | 9 | 7 | 7 | 1 | 3 | 3 | — | 5 |
| Lipoxol[6] | | | | | | 3 | — | — |
| Co-solvent (A) | | | | | | | | |
| Solketal | — | 6 | — | — | — | 5 | 8 | 5 |
| Isosorbide dimethylether | — | — | 6 | 5 | 5 | — | — | — |
| Water (A) | 73 | 71 | 71 | 73 | 74 | 67 | 70 | 70 |

[1]Surfactant mixture (comprising 40-60% Trideceth-9, 20-40% PEG 40 Hydrogenated castor oil, and up to 5% Polysorbate-20) marketed by Barnet
[2]C8/C10 polyglycosides marketed by Oleon
[3]C8/C10 polyglucosides marketed by Seppic
[4]PPG-1-PEG-9 Lauryl Glycol Ether marketed by Cognis/BASF AG
[5]PEG 40 hydrogenated castor oil marketed by Cognis/BASF AG
[6]PEG 400 marketed by Sasol Olefins and Surfactants GmbH

TABLE 3

| Example | Skin feeling | Drying speed | Tackiness | Wetness | Greasiness |
|---|---|---|---|---|---|
| 1-1 (comparison) | − | + | − | − | + |
| 1-2 | ++ | ++ | ++ | + | ++ |
| 1-3 | +++ | ++ | +++ | ++ | ++ |
| 1-5 | + | ++ | ++ | + | ++ |
| 1-7 | + | + | + | − | ++ |

+++: very good
++: good
+: acceptable
−: not acceptable

As can be seen from the test results above, all formulations containing the co-solvents showed better performance.

The invention claimed is:

1. An aqueous oil in water micro-emulsion consisting of:
   i) an odoriferous oil phase
   ii) at least one non-ionic surfactant
   iii) at least one co-solvent selected from the group consisting of: isosorbide, isosorbide ethers, solketal, solketal ethers, and mixtures thereof,
   iv) optionally, at least one solubilizer selected from the group consisting of: glycerol derivatives and diols, and mixtures thereof, and,
   wherein the micro-emulsion comprises up to 15% wt. of the odoriferous oil phase, and at least 65% wt. of water.

2. An aqueous oil in water micro-emulsion according to claim 1 wherein the at least one non-ionic surfactant has a HLB of 8 to 18.

3. A consumer product comprising an aqueous oil in water micro-emulsion according to claim 2.

4. An aqueous oil in water micro-emulsion according to claim 1 wherein the at least one co-solvent is selected from the group consisting of:
   a compound of formula (A)

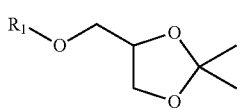

wherein $R^1$ is hydrogen, methyl, ethyl, $C_3$-$C_5$ alkyl, or $C_2$-$C_5$ hydroxy alkyl; and,
   a compound of formula (B)

(B)

wherein $R^2$ and $R^3$ are independently of each other selected from hydrogen, methyl, ethyl, $C_3$-$C_5$ alkyl, and $C_2$-$C_5$ hydroxy alkyl.

5. An aqueous oil in water micro-emulsion according to claim 1 wherein the at least one co-solvent is selected from the group consisting of: isosorbide, solketal, 4-(methoxymethyl)-2,2-dimethyl-1,3-dioxolane, 4-(ethoxymethyl)-2,2-dimethyl-1,3-dioxolane, 3,6-dimethoxyhexahydrofuro[3,2-b]furan, and mixtures thereof.

6. An aqueous oil in water micro-emulsion according to claim 1 wherein the at least one solubilizer is selected from the group consisting of: 1, 2- propanediol, 1, 3 - propanediol, 1, 2-pentandiol, 2-methyl-pentan-2,4-diol, 1,2-hexanediol, 1,2-octanediol, dipropylene glycol propyl ether, dipropylene glycol isobornylether, and mixtures thereof.

7. A consumer product comprising an aqueous oil in water micro-emulsion according to claim 1.

* * * * *